United States Patent
Blondeau et al.

(10) Patent No.: US 6,752,958 B2
(45) Date of Patent: Jun. 22, 2004

(54) DISINFECTING WOODEN ELEMENTS IN CONTACT WITH FOODSTUFFS

(75) Inventors: Eric Blondeau, Biarritz (FR); Sophie Berthelot, Begles (FR)

(73) Assignee: Thatles International, Canejan (FR)

( * ) Notice: Subject to any disclaimer, the term of this patent is extended or adjusted under 35 U.S.C. 154(b) by 0 days.

(21) Appl. No.: 10/221,413

(22) PCT Filed: Mar. 8, 2001

(86) PCT No.: PCT/FR01/00693

§ 371 (c)(1),
(2), (4) Date: Sep. 10, 2002

(87) PCT Pub. No.: WO01/68153

PCT Pub. Date: Sep. 20, 2001

(65) Prior Publication Data

US 2003/0049162 A1 Mar. 13, 2003

(30) Foreign Application Priority Data

Mar. 10, 2000 (FR) ............................ 00 03079

(51) Int. Cl.$^7$ ............................ A61L 2/00; C12N 13/00
(52) U.S. Cl. ...................................... 422/22; 435/173.1
(58) Field of Search ......................... 422/22; 435/173.1

(56) References Cited

FOREIGN PATENT DOCUMENTS

| | | |
|---|---|---|
| DE | 198 02 297 C1 | 7/1996 |
| GB | 1126233 | 9/1999 |

*Primary Examiner*—Christopher R. Tate
*Assistant Examiner*—Randall Winston
(74) *Attorney, Agent, or Firm*—James Ray & Associates

(57) ABSTRACT

The invention relates to a method and a plant for disinfecting at least one wooden container (10) likely to have been contaminated by microorganisms. It comprises treatment means for submitting said container to the action of an electromagnetic field, the frequency of which is between 1 MHz and 300 GHz, so as to destroy at least part of the population of microorganisms contained in said cask.

7 Claims, 2 Drawing Sheets

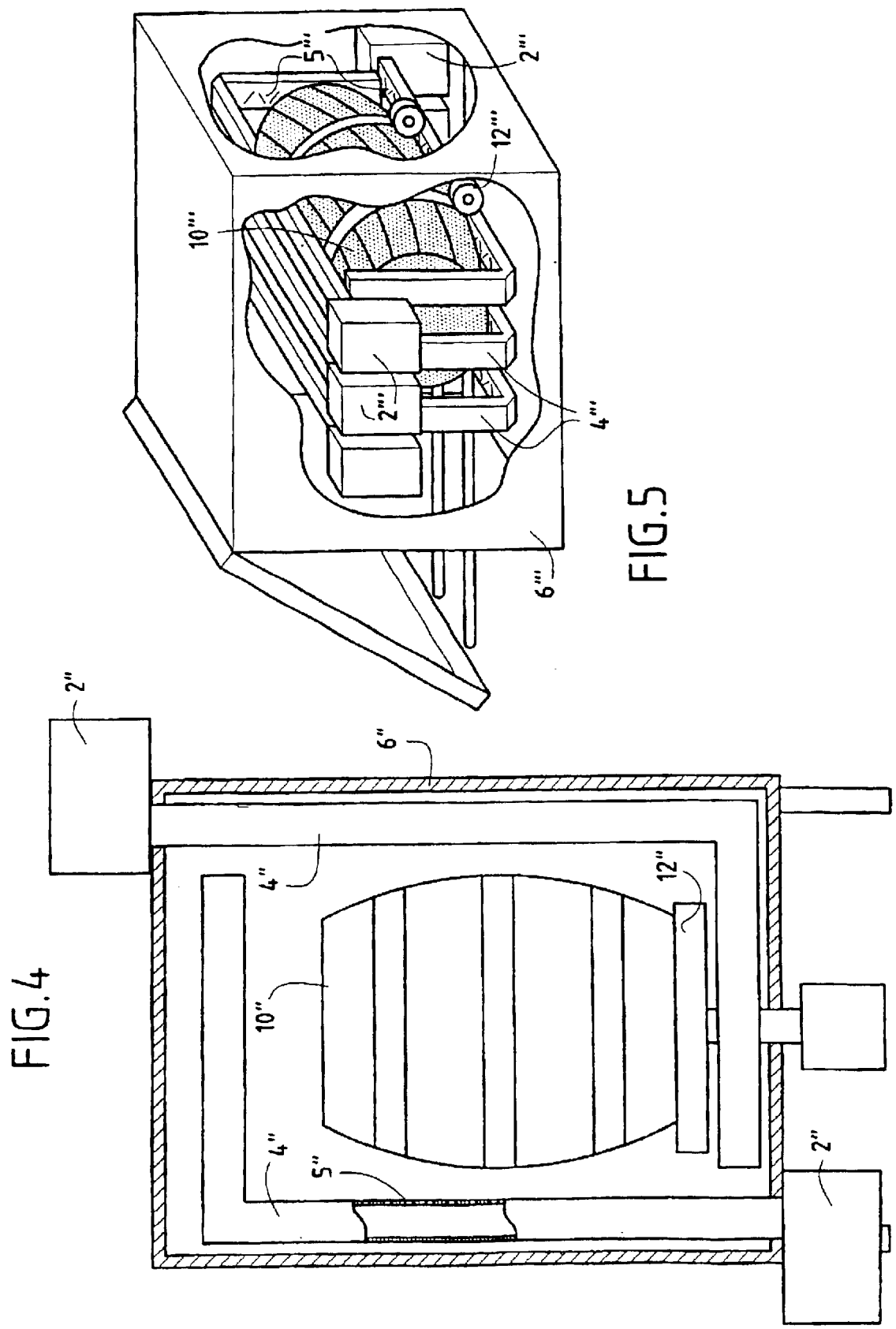

DISINFECTING WOODEN ELEMENTS IN CONTACT WITH FOODSTUFFS

Figure 1:
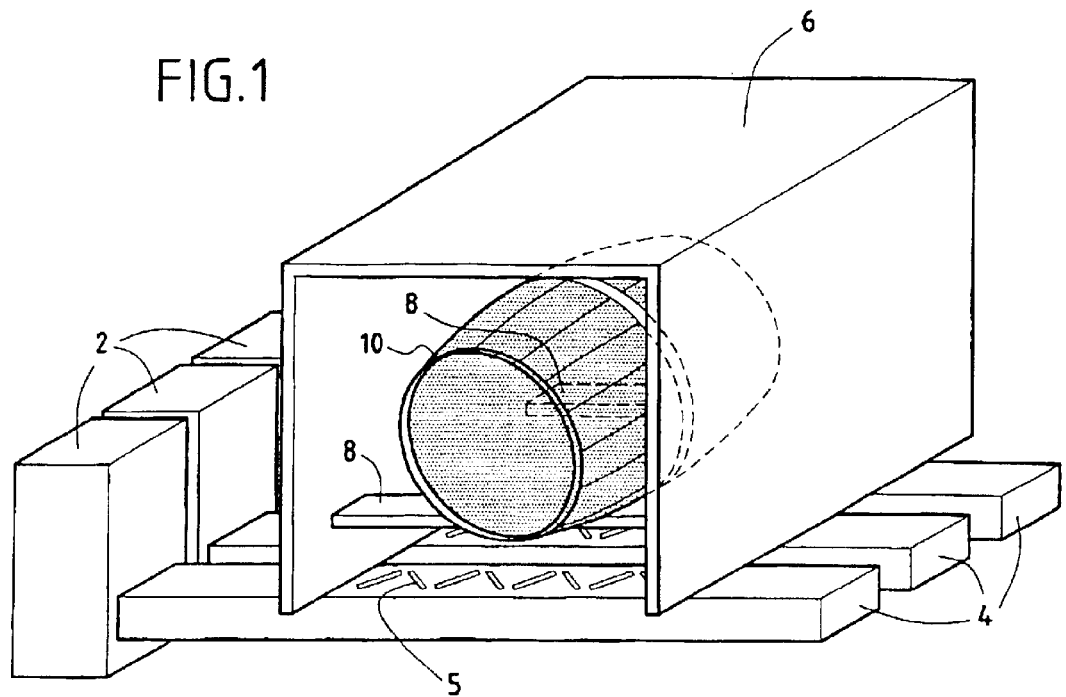

The present invention relates to a method and plant for disinfecting a wooden container likely to have been contaminated by microorganisms during its use.

The envisioned field of application is especially, but not exclusively, that of sterilizing casks intended for aging wine or casks likely to contain foodstuffs.

Generally, wine ages in a cask for a period during which the components of the wine diffuse and react with the wood of the inner wall and the deeper layers of the cask. Next, the wine is removed and deposits may remain on the inner wall of the cask. For it to be used again, in a similar or identical application, the cask must be reconditioned, in order to remove any deposits, then disinfected.

The reconditioning consists in cleaning the inner walls of the cask and then in disinfecting it in order to obtain a satisfactory sanitary condition and optimum preservation of the casks.

Usually, the inside of the casks is disinfected or sterilized by the action of steam, which may be injected under pressure and held inside for a predetermined time. Thus, the heat energy destroys the microorganisms located in the cask. However, the destruction takes place with some time lag, given the thermal inertia of the cask walls, and hampers the efficiency of the method. In order to accelerate the disinfection rate, it is possible to increase the steam pressure in the cask, but this runs the not inconsiderable risk of explosion and/or increases the thoroughness with which the inner walls of the cask are washed.

Another drawback of sterilization by steam is that it contributes to swelling the wood which absorbs the water and makes it more malleable.

One object of the present invention is to propose a method of disinfecting wood likely to have been contaminated by microorganisms while avoiding the drawbacks connected with the use of steam.

To achieve this aim, according to the invention, the method of disinfecting a wooden container likely to have been contaminated by microorganisms is characterized in that said container is subjected to the action of an electromagnetic field, the frequency of which is between 1 MHz and 300 GHz, in order to destroy at least part of the population of microorganisms contained in said cask.

The action of the electromagnetic field throughout the frequency range from 1 MHz to 300 GHz produces oscillation of the polar molecules or of the ions which, by friction, causes heating of the material. Heat transfer by conduction plays a secondary role within the substance, unlike other heating techniques, but it equalizes the temperature locally.

The frequencies used have the advantage of involving radiation whose penetration is a few centimeters while penetration of the infrared radiation, the wavelength of which is between $10^{-3}$ m and $10^{-6}$ m and which is commonly used to heat material, is a few millimeters. Consequently, it is possible to cause heating of the inner surface of the wall, when it is a few centimeters thick, by friction of the polar molecules or of the clusters, virtually at any point and at the same time. In this way, the microorganisms attached to the inner surface of the container wall are destroyed by the action of the radiation, which makes it possible to increase the temperature of the environment of the microorganisms.

Preferably, the wooden container is a wooden cask intended to contain alcohols or foodstuffs. These casks consist of longitudinal wooden elements hermetically fastened to each other in order to form a container having cylindrical symmetry and retained by hoops which are usually metallic, the two ends of the container being closed by flat fonts [sic]. Although the presence of the metal hoops prevents it being possible to envision treating the casks with suitable electromagnetic radiation, which would cause electric arcs detrimental to the treatment and especially local heating likely to damage the wall, it turns out that the inner surface of the cask wall heats without electric arcs appearing at the metal hoops. Thus treating wooden casks by means of suitable electromagnetic radiation leads to optimum sterilization of its inner wall, on the one hand, which is in direct contact with the liquid which it is likely to contain, and of the whole cask, on the other hand. Although a cask is a closed container, the thickness of its wall being a few centimeters, the radiation produces an effect on its inner surface.

Apart from the direct action on the microorganisms, the radiation acts on their environment and, in particular, on the water which is inevitably present in relatively large quantities on or in the wall and which is a prime example of a polar molecule. The friction of the water molecules produces an increase in the temperature also contributing to degrading the microorganisms.

According to a preferred implementational mode, the frequency of the electromagnetic field is between 865 MHz and 5850 MHz, which corresponds to microwaves.

According to a particular feature, the wooden container can be moved with respect to an electromagnetic source so that the action of said field on said container is uniform. Thus the hot spots, separated by a half wavelength, which occur when an object is irradiated, are attenuated by conduction since the container can be moved with respect to the source.

According to another particular feature, the electromagnetic source can be moved with respect to said wooden container so as to be able to treat wooden containers which are fixed or too bulky to be transported, as is for example the case for vats and barrels, and to solve the problem of homogenizing the temperature within the container.

According to a third particular feature, an electromagnetic field of 2450 MHz plus or minus 25 MHz, the power output of which is greater than 5 kW, is applied for a time at least equal to 300 s for a standard container. Thus the amount of energy applied to the wooden container is enough to destroy at least part of the population of microorganisms contained in said cask.

Another object of the present invention is to supply a plant for sterilizing or for disinfecting at least one wooden container likely to have been contaminated by microorganisms during its use. The plant comprises treatment means in order to subject said container to the action of an electromagnetic field, the frequency of which is between 1 MHz and 300 GHz, so as to destroy at least part of the population of microorganisms contained in said cask.

Advantageously, the treatment means comprise at least one electromagnetic wave generator extended by an applicator which is connected thereto capable of making said waves interact with said wooden container. The applicator consists of a slot antenna forming a wave guide in order to make the waves interact accurately on the wooden container.

Preferably, the plant comprises a plurality of electromagnetic wave generators extended by waveguides which at least partially surround said wooden container. This arrangement makes it possible to treat the wooden container from several angles simultaneously and leads to a substantially uniform application over the surfaces of the container.

According to a particular characteristic of the invention, the plant comprises electromagnetic wave generators emitting waves whose frequency is between 1 MHz and 300 GHz and having a power output at least equal to 1 kW.

These features make it possible to destroy the microorganisms since the heat energy resulting from the action of the waves exceeds a value beyond which they cannot survive.

According to another particular feature, support means are provided located close to the waveguides and capable of supporting said wooden container.

Advantageously, the support means can be moved in order to displace said wooden container with respect to the waveguides so as to homogenize the action of the waves on said container and to treat the container uniformly.

According to a particular implementational mode, the treatment means can be moved with respect to said container for uniform treatment or so that they can be transported to the user site for fixed wooden containers.

Figure 2:
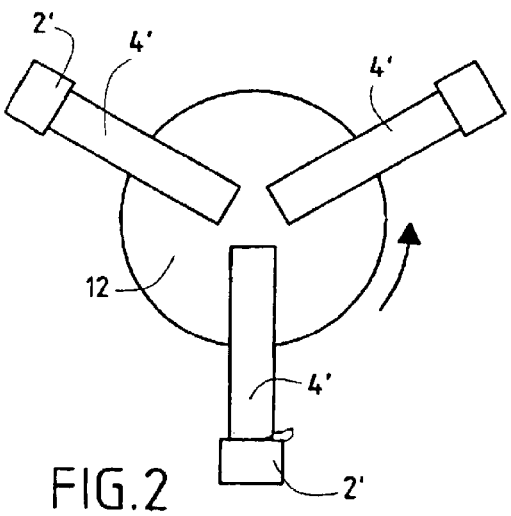
Figure 3:
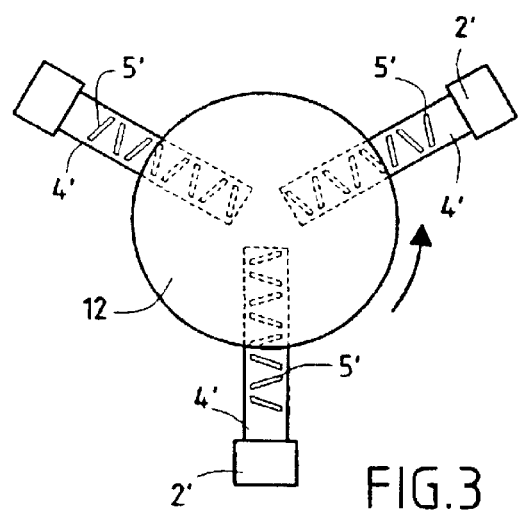

Other particular features and advantages of the invention will become apparent on reading the following description of particular nonlimiting embodiments of the invention, given by way of example, with reference to the appended drawings in which:

FIG. 1 is a perspective view showing a plant according to a particular implementational mode in which three generators fitted with three parallel waveguides are installed, FIG. 2 is a bottom view showing a plant according to another particular embodiment in which three waveguides are mounted at 120° to each other in the same plane, FIG. 3 is a top view showing the plant according to the embodiment of FIG. 2, FIG. 4 is a front view showing a plant according to a further embodiment in which a cask is placed between two vertical waveguides, and, FIG. 5 is a perspective view showing a plant according to a fourth embodiment in which a cask is placed between three pairs of waveguides, each one in line with a generator.

First of all, with reference to FIG. 1, a plant for implementing the method according to the invention will be described.

The plant comprises three wave generating blocks 2 extended by three waveguides 4. The wave generating blocks 2 consist of a magnetron capable of producing microwaves, the frequency of which is 2450 MHz plus or minus 25 MHz. This frequency is not limiting and any other frequency could be envisioned provided standards in force are complied with, or that a completely isolated plant is designed.

The block 2 also comprises heat protection for the magnetron so as to prevent the risk of damage by too great an increase in temperature.

The power output of the magnetron, capable of producing waves whose frequency is 2450 MHz plus or minus 25 MHz, is 1.2 kw but it is in no way limiting and may be adapted according to the treatment envisioned.

The electromagnetic waves generated by the magnetron are directed into a cavity, called a waveguide 4, in which they are propagated. The cavities shown in FIG. 1 are provided with alternating slots 5 which the waves pass through in order to be propagated outside. These slots 5 have a particular shape and arrangement in order to prevent couplings and to optimize emission of the wave so as to prevent it returning to the generator. In particular, they are substantially and consecutively at 90° to each other.

The three waveguides 4 are placed in parallel and are contiguous so as to form a flat emitting surface.

The plant comprises a box 6 forming an electromagnetic barrier which is fastened to this flat surface and which can also be fitted with a suction device (not shown) capable of sucking the gases and the volatile substances that would be produced by the microwave treatment.

The box 6 has fixed supports 8 on which a wooden container 10 to be treated is supported. The type of wooden container likely to be subjected to the action of the microwaves for purposes of sterilization is extremely broad, but generally it involves containers used in the agro-food industry in which the proliferation of germs or of microorganisms absolutely must be limited.

Moreover, the microorganisms are likely to develop not only on the surfaces of the walls of the wooden containers but also in the deeper layers, which presents an additional difficulty with regard to the disinfection method compared to plastic or metal containers for which the proliferation of microorganisms essentially takes place on the surface.

When the microorganisms proliferate only on the surface, the treatment is easier and can be carried out by increasing the surface temperature of the container by steam or by any heat source.

On the other hand, for wood, where the microorganisms are likely to develop throughout the entire thickness, heat destruction is only achieved by increasing the temperature of the entire container. Now in the case of heating by infrared radiation or by steam, the penetration of which into the surface layers is low or zero, the temperature only increases within the core of the container by conduction, which requires a certain time.

Microwave radiation at 2450 MHz plus or minus 25 MHz has the advantage of being much more penetrating than infrared radiation and penetrates a thickness of a few centimeters. Thus for a wooden container whose thickness is of the same order of magnitude, any microorganism population, whatever its depth, is substantially destroyed by heating its environment.

This destruction proceeds from the indirect action of heating polar compounds surrounding the microorganisms. The wooden containers placed in normal atmospheric conditions have a substantial moisture level, and it is mainly water which is also heated in the wood and which contributes to the heat destruction of the microorganisms.

The internal heating of the wooden container may produce steam which causes an internal overpressure increasing the heat effect and therefore the action on the microorganisms.

In FIG. 1, the wooden container 10 consists of a wooden cask intended to contain wine or any other liquid foodstuff. After it has been placed on the supports 8, the wooden container 10 is subjected to the action of the microwaves by bringing the magnetrons into service, producing radiation which propagates in the waveguides 4 and which passes through the slots 5 to act under said container 10. The waves pass through the wall of the container such that they heat it throughout its bulk, and in particular its internal surface, such that all the microorganisms contained in said cask are likely to be affected and therefore destroyed.

With reference now to FIG. 2 and FIG. 3, a particular implementational mode of the plant will be described, which takes account of the problems of discontinuity of heating which the microwave treatment may bring.

This is because, in the previous plant, the wooden container 10 is static with respect to the source and the bulky containers are unequally subjected to radiation which produces regions of different temperatures.

To overcome this drawback, a plate 12 transparent to microwaves fitted with a device for driving in rotation and/or in translation, is placed above the waveguide 4' facing the slots 5'. Three waveguides 4' are placed in a star arrangement in the same plane making an angle of 120° to each other. The generator blocks are not shown but they are fixed to the end of the three waveguides 4' forming the star.

The container to be treated is placed on the surface 14 of the rotating plate 12 which is rotated while the wave generators are in operation. The waves which pass through the slots 5' also pass through the rotating plate 12, which is generally made of Teflon® and transparent to microwaves, in order to act on the wooden container (not shown) placed on the surface 14 of the rotating plate 12.

The waves are propagated in constant directions, and the rotation of the wooden container makes it possible to vary the angle of incidence of the waves throughout its entire volume, and therefore to homogenize the action of the electromagnetic field on the entire wooden container.

According to another particular embodiment, for which reference should be made to FIG. 4, a plant intended for sterilizing wooden casks for storing wine or any other food product will be described.

The plant comprises a metal chamber 6", in which two waveguides 4 are placed vertically against two opposed walls with the slots 5" facing each other and to the upper end of which are fastened wave generating blocks 2". A rotating plate 12" is connected to the base of the chamber 6" via a device capable of rotating it.

A cask 10" is placed vertically on the rotating plate 12" between the two waveguides 4" and it is rotated while the generators 2" are in operation. Consequently, as in the previous embodiment, the angle of incidence of the waves throughout the entire volume of the cask 10" varies with its movement and allows thermal homogenization.

The casks used for aging wine have certain types of microorganisms, the majority of whose populations must be destroyed. These microorganisms are acetic bacteria, for example Acetobacter, yeasts, for example Brettanomyces, lactic bacteria, for example Pediococcus or various molds of the Penicillium type, or else any other organism which persists after removing the wine and which is likely to line the inner surface of the cask 10" and the deeper layers.

Microwaves are perfectly suitable for destroying microorganisms developing inside the cask 10" since the radiation is sufficiently penetrating to act on its inner surface. Moreover, the entire volume of the wall of the cask 10" is subjected to the radiation, consequently, any contaminating agent present inside the wall can be reached.

According to a third particular implementational mode of the invention, illustrated in FIG. 5, the plant comprises six wave generating blocks 2''', each one being fitted with a waveguide 4''' forming an "L". The waveguides 4''' and their generating blocks are combined in pairs so as to form a quadrilateral, the three pairs being juxtaposed so as to constitute a parallelepiped capable of surrounding a horizontal cask 10''' having a capacity of 225 liters in the standard case.

The waveguides comprise slots 5''' directed toward the cask 10''' on the inner faces of the two branches of waveguides forming an "L".

The plant also has two pairs of rollers 12''', on which the cask 10''' is placed, they are rotated by motorization so as to drive the cask 10''' about its main axis while the generators are in service.

The device as a whole is surrounded by a chamber 6''' so as to contain the electromagnetic waves generated by the magnetrons.

To illustrate the invention according to the embodiment previously described, an example of operating conditions is given by way of illustration.

Casks to be treated, the capacity of which is between 200 and 600 liters, have a hygrometry between 10 and 50%; they have been used for aging alcohol and they are treated in order to be reused.

Initially, they are cleaned with water possibly containing detergent products then they are introduced, one by one, into the plant described above.

Each of the generators has a power of 1.2 kW and the frequency at which they operate is 2450 MHz plus or minus 25 MHz. The treatment time is 900 seconds and the temperature of the inner surface of the cask is between 65 and 95° C. while the internal temperature of the wall of the cask is between 50 and 90° C.

Under these operating conditions, the populations of microorganisms initially contained in the casks were destroyed and made it possible to obtain a disinfected cask capable of being used again for the storage of wine.

For all the embodiments described above, provision is made to be able to adapt the plant for additional thermal means capable of supplying extra heat energy to said wooden container. This energy is likely to be supplied by steam or any other means. This addition is even more beneficial to provide supplementary treatment over any wooden part located under the metal hoops.

Moreover, the wave generator is capable of emitting pulsed or continuous waves.

What is claimed is:

1. A method for disinfecting wooden casks forming a closed container having a wall with an inner surface and contaminated by micro-organisms, said method comprising the step of subjecting said wooden cask to the action of an electromagnetic field, the frequency of which is between 1 MHz and 300 GHz, whereby the inner surface of said wall of said wooden cask is reached with said electromagnetic field and at least part of said micro-organisms contained in said cask are destroyed.

2. The disinfection method as claimed in claim 1, wherein said wooden cask consists of elongate wooden elements hermetically attached to each other and retained by metal hoops.

3. The disinfection method as claimed in claim 1, wherein said frequency of the electromagnetic field is between 865 MHZ and 5850 MHz.

4. The disinfection method as claimed in claim 1, wherein the step of subjecting said wooden cask to an electromagnetic field comprises the steps of supplying an electromagnetic source and moving said cask with respect to said source whereby said cask is substantially uniformly subjected to said electromagnetic field.

5. The disinfection method as claimed in claim 1, wherein the step of subjecting said cask to said electromagnetic field comprises the steps of providing an electromagnetic source and moving said source with respect to said wooden cask.

6. The disinfection method as claimed in claim 1, wherein said cask is subjected to an electromagnetic field of 2450 MHz plus or minus 25 MHz, the power output of which is greater than 5 kW, for a time at least equal to 300 s.

7. The disinfection method as claimed in claim 6, wherein said wooden cask consists of elongate wooden elements and metal loops for hermetically attaching said elements to each other.

* * * * *